United States Patent
Mizushima et al.

(10) Patent No.: US 6,190,694 B1
(45) Date of Patent: Feb. 20, 2001

(54) CHITOSAN-CONTAINING SOFT CAPSULE AND PROCESS FOR PRODUCING THE SAME

(75) Inventors: Yutaka Mizushima, Tokyo; Yasuo Kosaka, Matsudo; Toshio Satoh, 57-3, Nagao, Joroku-cho, Tokushima-city Tokushima-pref., all of (JP)

(73) Assignees: Toshio Satoh; LTT Institute Co., Ltd.; V-Tec Co., Ltd., all of (JP)

( * ) Notice: Under 35 U.S.C. 154(b), the term of this patent shall be extended for 0 days.

(21) Appl. No.: 09/416,183

(22) Filed: Oct. 11, 1999

(30) Foreign Application Priority Data

Apr. 5, 1999 (JP) .................................................. 11-098146

(51) Int. Cl.$^7$ ............................... A61K 9/48; A61K 9/00; A61K 9/14
(52) U.S. Cl. ......................... 424/451; 424/400; 424/450; 424/451; 424/489
(58) Field of Search ................................. 424/450, 451, 424/400, 489, 442, 452

(56) References Cited

U.S. PATENT DOCUMENTS 4,533,557 * 8/1985 Maruyama et al. .................... 426/61
5,468,503 * 11/1995 Yamada et al. ....................... 424/461
5,720,793 * 2/1998 Katoh et al. ............................ 71/16
5,770,187 * 6/1998 Hasebe et al. ......................... 424/69

FOREIGN PATENT DOCUMENTS 09110634    4/1997  (JP) .

OTHER PUBLICATIONS

Journal of Traditional Medicines,11, 198–205, 1994.

* cited by examiner

Primary Examiner—Thurman K. Page
Assistant Examiner—S. Tran
(74) Attorney, Agent, or Firm—Price, Heneveld, Cooper, DeWitt & Litton

(57) ABSTRACT

The present invention relates to a process for producing a chitosan-containing soft capsule. The process includes the steps of rendering chitosan a powder; adding the chitosan powder, powder comprising an organic acid and a salt thereof, and an emulsifier to an oil or fat; stirring the resultant mixture so as to suspend the powders, to thereby obtain a gel-like stock; and feeding the gel-like stock and a gelatin solution for coating into an automated encapsulation machine, to effect encapsulation of the stock with gelatin.

12 Claims, 6 Drawing Sheets

DIFFERENCES IN SYSTOLIC BLOOD PRESSURE BETWEEN THE CASE OF ADMINISTRATION OF A CUTTLEFISH-CHITOSAN SOFT CAPSULE AND THE CASE OF ADMINISTRATION OF A PLACEBO (LEFT: IN THE MORNING, RIGHT: AT NIGHT)

CASE NO. (** < 0.01, * < 0.05)

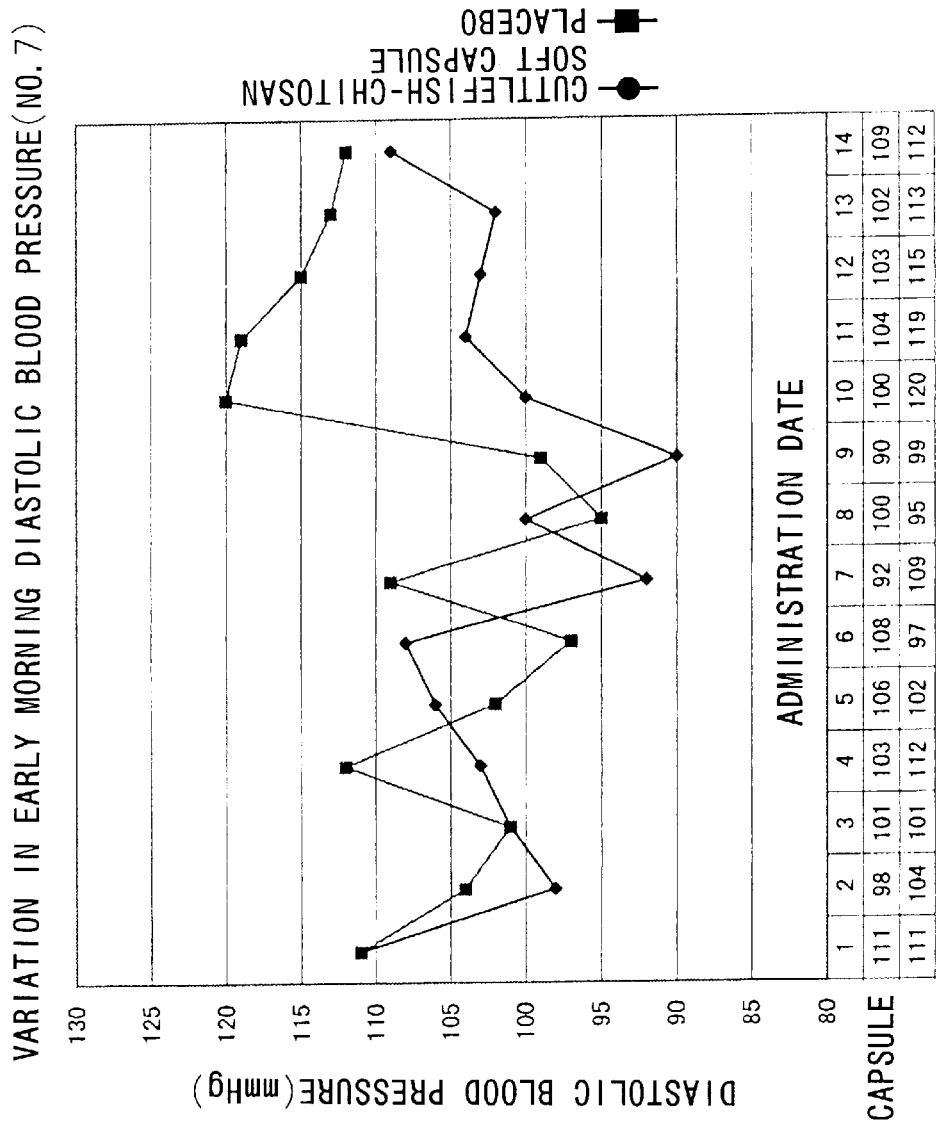
F I G. 5

CHITOSAN-CONTAINING SOFT CAPSULE AND PROCESS FOR PRODUCING THE SAME

BACKGROUND OF THE INVENTION

1. Field of the Invention

The present invention relates to soft capsules which encapsulate chitosan therein (hereinafter may be referred to as "chitosan soft capsules"). The chitosan soft capsules of the present invention are advantageously used for controlling blood pressure of hypertensives. The present invention also relates to a process for producing the soft capsules.

2. Background Art

Hypertension; in particular, essential hypertension having no underlying disease, induces lethal diseases of organs such as the heart, brain, and kidneys. Therefore, daily control of blood pressure to a normal state is a key to curing diseases induced by hypertension. A variety of antihypertensive drugs have been developed and employed for treating hypertension. However, such drugs induce adverse side effects such as headache, drowsiness, cough, and depression. Therefore, patients taking such drugs during treatment become de-energized or feel weak, and may suffer degraded quality of life (QOL).

Extensive studies have been carried out for reducing blood pressure without use of conventional drugs. One such study is application of chitosan.

Presently it is well known that chitosan has an antihypertensive effect and that hypertension is caused by excess intake of salt. See, for example, OKUDA et al., *Journal of Traditional Medicine* 11, 198–205, 1994 (Hideo KATO, Tomoko TAGUCHI, Hiromichi OKUDA, Mari KONDO, and Minoru TAKARA).

In the above journal, OKUDA et al. describe that in the digestive tract chitosan captures chloride ions ($Cl^-$) originating from salt contained in ingested food and excretes the ions into feces, to thereby exhibit an action for reducing blood pressure. Briefly, $Cl^-$ in blood activates an angiotensin-converting enzyme (ACE) which acts to elevate blood pressure, whereas chitosan promotes excretion of chloride ions ($Cl^-$) into feces, to thereby suppress transfer of $Cl^-$ into blood and reduce blood pressure. A test conducted by OKUDA et al. revealed that intake of chitosan powder in an amount of 5 g per day suppresses human hypertension caused by a high-salt diet.

However, the present inventors have observed that intake of an aqueous solution of cuttlefish-chitosan containing chitosan in an amount as small as 20 mg is effective in reducing blood pressure of hypertensives (see Tests 1 through 5 described below). According to the calculation described by OKUDA et al. the amount of salt captured by 20 mg of chitosan is about 6 mg, and the capture of salt in such a small amount is unlikely to reduce blood pressure. Thus, the present inventors considered that the mechanism of inhibiting $Cl^-$-intake attributed to chitosan is not a direct capture but involves inhibition of the $Cl^-$ absorption process, such as $Cl^-$ channeling. When channeling-like inhibition occurs, chitosan should manifest its action in an aqueous solution state, and administration of solid state chitosan would provide only poor inhibition efficiency.

In their test, OKUDA et al. administered solid chitosan derived from a crab in an amount as large as 5 g to human subjects. However, daily intake of such a large amount of chitosan from food or drugs is not realistic. As mentioned above, it was previously found that a small amount of chitosan was expected to provide an antihypertensive effect so long as it is used in the form of an aqueous solution. Along this line, studies on preparing an aqueous solution of chitosan have been carried out, and a patent application has been filed (Japanese Patent Laid-Open Publication No.110634/1997).

Briefly, there has been developed a method in which cuttlefish-chitosan having a deacetylation degree of 75% or more is dispersed in an aqueous alkali solution for hydration and an organic acid in an amount of 0.01–5 wt. % is added to the dispersion to thereby form a neutral solution.

In view of the foregoing, the present inventors have conducted a test, in which 1% aqueous solution of cuttlefish-chitosan in a volume of 1–3 ml (equivalent to 10–30 mg of chitosan) was administered to five hypertensive patients, and reduction of blood pressure was observed.

Test for an Effect on Reduction of Blood Pressure Induced by 1% Aqueous Solution of Cuttlefish-Chitosan (pH 5.5–6.0)

Case 1. Age 68, Female

When the subject took 2–3 ml of the cuttlefish-chitosan aqueous solution three times daily, systolic pressure was reduced from 180 mmHg to 150 mmHg. Thereafter, the dose was reduced to 2 ml or less twice daily and the administration was continued. Systolic pressure stabilized at 150 mmHg.

Case 2. Age 72, Male

When the subject took 5 ml of the cuttlefish-chitosan aqueous solution at one dose together with a cup of onion-infused wine, systolic pressure was drastically reduced from 190–200 mmHg to 160 mmHg. The reduction in blood pressure was so drastic that the dose of the solution was reduced to 2 ml and the administration was continued. Thereafter systolic pressure was gradually reduced from 180 mmHg to 170 mmHg and then to 160 mmHg, where it stabilized.

Case 3. Age 57, Male

When the subject took 3 ml cuttlefish-chitosan aqueous solution at one dose together with a cup of black mushroom broth, 2–3 times per day, systolic pressure was reduced from 180 mmHg to about 150 mmHg.

Case 4. Age 51, Male

When the subject took the cuttlefish-chitosan aqueous solution at a dose of 1 ml and five droplets of mixed propolis twice daily, systolic pressure was reduced from 170 mmHg to 150–155 mmHg.

Case 5. Age 46, Female

When the subject took the cuttlefish-chitosan aqueous solution at a dose of 2 ml twice daily, and the administration was continued, systolic pressure was gradually reduced from 150 mmHg to 130–135 mmHg.

In consideration of the above results, application of the cuttlefish chitosan aqueous solution to pharmaceuticals and health food has been studied. However, the cuttlefish-chitosan aqueous solution employs glutamic acid as an organic acid and sodium glutamate, and provides such bad taste that daily intake of the solution as such is difficult. Thus, encapsulation of the solution has also been studied. However, encapsulation of an aqueous solution is difficult in that capsules per se dissolve in water.

SUMMARY OF THE INVENTION

The present inventors have considered that development of pharmaceuticals or health foods which can be easily ingested by hypertensives in their daily life without worry about adverse side effects would be useful in treatment of hypertension, and have attempted to encapsulate a cuttlefish-chitosan aqueous solution, thus leading to completion of the invention.

In view of the foregoing, an object of the present invention is to provide a chitosan soft capsule. Another object of the present invention is to provide a process for producing the same.

Accordingly, in a first aspect of the present invention, there is provided a process for producing a chitosan-containing soft capsule comprising the following steps:

rendering chitosan into a powder;

adding the chitosan powder, powder comprising an organic acid and a salt thereof, and an emulsifier to an oil or fat;

stirring the resultant mixture so as to suspend the powders, to thereby obtain a gel-like stock; and feeding the gel-like stock and a gelatin solution for coating into an automated encapsulation machine, to effect encapsulation of the stock with gelatin.

In a second aspect of the present invention, there is provided a chitosan-containing soft capsule comprising a capsule enclosing a composition which contains chitosan powder and powder comprising an organic acid and a salt thereof which are suspended in an emulsifier-added oil or fat.

Preferably, the organic acid is an amino acid such as glutamic acid or aspartic acid; a hydroxycarboxylic acid such as glycolic acid, lactic acid, malic acid, citric acid, tartaric acid, gluconic acid, or ascorbic acid; or a pyrrolidonecarboxylic acid such as pyroglutamic acid.

Preferably, the organic acid and the salt are glutamic acid and sodium glutamate.

Preferably, the oil or fat is soybean oil, sesame oil, olive oil, rapeseed oil, cottonseed oil, rice oil, corn oil, evening primrose oil, safflower oil, palm oil, castor oil, sardine oil, herring oil, cod oil, shark oil, cuttlefish oil, whale oil, dolphin oil, roach oil, carp oil, eel oil, hyperoratia oil, euphausian oil, chrysalis oil, lard, or beef tallow.

Preferably, the chitosan is derived from cuttlefish.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with the accompanying drawings, in which:

FIG. 5 is a graph showing variation in early morning diastolic blood pressure of case No. 7 in Table 1.

DETAILED DESCRIPTION OF PREFERRED EMBODIMENTS

Figure 1:
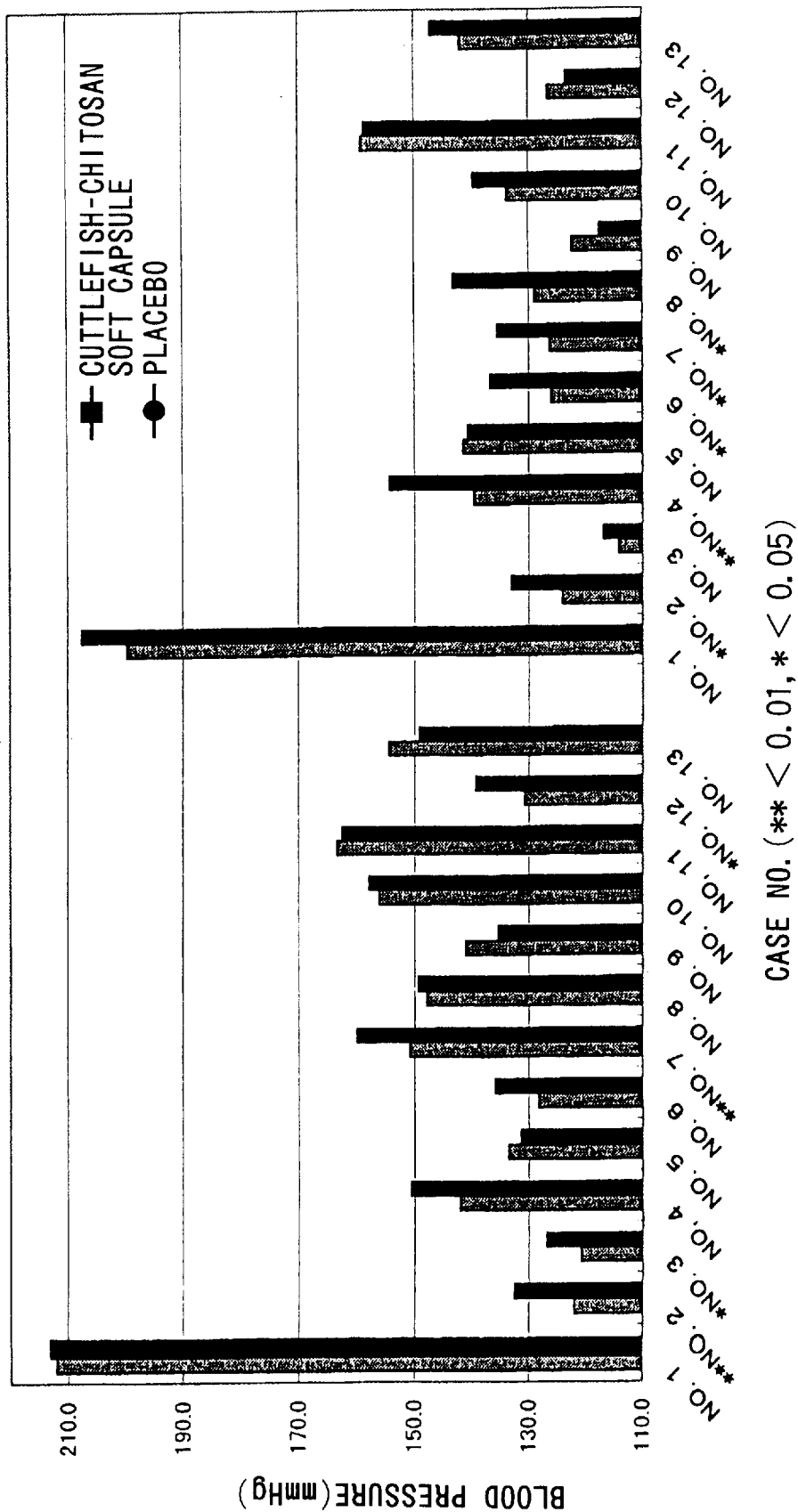
FIG. 1 is a graph showing differences in systolic blood pressure between the case of administration of a cuttlefish-chitosan soft capsule and the case of administration of a placebo.

The present inventors have developed a soft capsule filled with a suspension prepared by suspending cuttlefish-chitosan powder and powder comprising an organic acid and a salt thereof into an oil or a fat to which an emulsifier had been added. The capsule is intended to provide the following effect. Briefly, when a human subject ingests the capsule, in the digestive tract, the capsule itself dissolves to release cuttlefish-chitosan enclosed in the capsule. The released cuttlefish-chitosan first comes into contact with a small amount, i.e., 0.5–1.0 ml, of digestive juice. As mentioned above, the present inventors have already succeeded in imparting water solubility to cuttlefish-chitosan by use of a 0.01–5 wt. % solution of an organic acid. Therefore, it is assumed that a solution with which cuttlefish-chitosan comes into contact in the digestive tract imparts water solubility to cuttlefish-chitosan in the presence of an organic acid and an organic acid salt, within the organic acid concentration range of about 5 wt. % and 0.01 wt. %. In order to satisfy this condition, the amount of the organic acid per capsule is 25–50 mg.

The chitosan which is used in the soft capsule of the present invention may be chitosan obtained from a calcified internal shell of a cuttlefish. Powder of a calcified internal shell, or cuttlebone, of cuttlefish that predominantly comprises chitin is produced by collecting cuttlebones from a cuttlefish, washing and drying the cuttlebones, and crushing the dried matter. The powder is treated with an alkaline solution, to thereby obtain cuttlefish-chitosan powder having a deacetylation degree of 85% or more. No particular limitation is imposed on the organic acid and a salt thereof so long as they can dissolve cuttlefish-chitosan. Examples thereof which may be used in the present invention include amino acids such as glutamic acid and aspartic acid; hydroxycarboxylic acids such as glycolic acid, lactic acid, malic acid, citric acid, tartaric acid, gluconic acid, and ascorbic acid; and pyrrolidonecarboxylic acids such as pyroglutamic acid. Soybean oil and other oils or fats may be used as the oil or fat in which cuttlefish-chitosan and the organic acid and salt thereof are suspended. Typically, oils or fats which are food or drugs for humans and animals may be used, and the form and components thereof are not limited. Preferred examples include C4–C24 saturated and unsaturated fatty acids and esters thereof, phospholipids containing these fatty acids, and animal and vegetable oils and synthetic oils containing these fatty acids and mixtures thereof.

More specifically, examples of the saturated fatty acids include palmitic acid, stearic acid, lauric acid, and myristic acid. Examples of the unsaturated fatty acids include palmitoleic acid, oleic acid, linoleic acid, linolenic acid, eicosapentanoic acid, docosahexanoic acid, and arachidonic acid. Examples of the animal oils include sardine oil, herring oil, cod oil, shark oil, cuttlefish oil, whale oil, dolphin oil, roach oil, carp oil, eel oil, hyperoratia oil, euphausian oil, chrysalis oil, lard, and beef tallow. Examples of the vegetable oils include soybean oil, sesame oil, olive oil, rapeseed oil, cottonseed oil, rice oil, corn oil, evening primrose oil, safflower oil, palm oil, and castor oil.

By use of a stirring apparatus, cuttlefish-chitosan and powder of an organic acid and salt thereof are sufficiently suspended in an oil or a fat incorporating an emulsifier, to thereby obtain a stock. Properties and viscosity of the stock are measured. The liquid and a gelatin solution for coating are fed into an automated encapsulation machine, to thereby fill capsular shells, i.e., to perform soft-encapsulation. During the step, the mold employed in the machine, moisture, temperature, air-flow, coating weight, content weight, coating thickness, and adhesion interface should be sufficiently controlled. Capsules filled with the stock are dried through two sets of drying steps in which drying time, temperature, and moisture are controlled. Subsequently, the dried capsules are subjected to a finishing step. All the soft capsules are inspected for appearance, and subjected to product inspection of items including characteristics, weight, dimensions, and water content. The soft capsules which have satisfactorily passed inspection are packaged and shipped.

EXAMPLES

The present invention will next be described in detail by way of examples and test examples.

Example

Production of Cuttlefish-Chitosan Soft Capsules

Cuttlefish-chitosan (207 g), glutamic acid (103.5 g), and sodium glutamate (207 g) were sufficiently mixed and added to soybean oil (1242 g). Monoglyceride (155.25 g) and beeswax (155.25 g) were added to the mixture and the resultant mixture was sufficiently stirred, to thereby obtain a white, gel-like stock. The stock and a gelatin solution for coating were fed into an automated encapsulation machine, to thereby produce about 6900 cuttlefish-chitosan soft capsules.

Test Example 1

Solubility of Cuttlefish-Chitosan Soft Capsules in Artificial Intestinal Juice (1) Solubility of cuttlefish-chitosan soft capsules in artificial gastric and artificial intestinal juice was studied.

Method: Ten cuttlefish-chitosan soft capsules (300 mg as reduced to cuttlefish-chitosan) produced in the above Example were added to 100 ml of artificial gastric juice and 100 ml of artificial intestinal juice, respectively, and the resultant mixtures were stirred at 37° C. for 30 minutes. The mixtures were centrifuged at 2000 rpm for 10 minutes at room temperature to thereby remove lipids, and then filtered with suction by use of a glass filter. The glass filter was heated at 105° C. for 3 hours, and weighed to thereby measure the weight of insoluble cuttlefish-chitosan.

Results: Cuttlefish-chitosan in soft capsules dissolved in the artificial gastric juice was 267.9 mg (89.3%) and cuttlefish-chitosan dissolved in the artificial intestinal juice was 133.8 mg (44.6%).

(2) In order to establish conditions similar to in vivo conditions, cuttlefish-chitosan was first stirred in a glutamate buffer, and artificial intestinal juice was gradually added to the buffer until the pH of the solution reached 6.6. Solubility of the cuttlefish-chitosan in the solution was measured.

Method: To a solution of sodium glutamate (1.0 g) dissolved in distilled water (50 ml), yaegaki-chitosan (deacetylation degree: 98.89%) (1.0 g) was added, and the mixture was stirred. A glutamic acid solution (about 1.4%) was gradually added to the mixture, and artificial intestinal juice was gradually added to the mixture. When the pH of the solution reached 6.6, precipitation of cuttlefish-chitosan was observed. The degree of precipitation was measured through heating gravimetric analysis. Solubility of cuttlefish-chitosan powder added to each of the artificial gastric juice and the artificial intestinal juice was measured as a control.

Results: The amount of cuttlefish-chitosan dissolved in the glutamate buffer was 87.0% of added cuttlefish-chitosan. When the artificial intestinal juice was added until the pH of the solution reached 6.6, the ratio was 90.2%. When only cuttlefish-chitosan powder was added to each of the artificial gastric juice and the artificial intestinal juice, 100% of the cuttlefish-chitosan was dissolved in the artificial gastric juice, whereas only 2.8% of the cuttlefish-chitosan was dissolved in the artificial intestinal juice.

(3) Solubility test of cuttlefish-chitosan was carried out by use of L-aspartic acid instead of glutamic acid.

Method: Yaegaki-chitosan (deacetylation degree: 98.89%) (1.0 g) was added to a solution of sodium L-aspartate (1.0 g) dissolved in distilled water (50 ml), and the mixture was stirred. An L-aspartic acid solution (about 1.4%) was gradually added to the mixture, and artificial intestinal juice was gradually added thereto. When the pH of the solution reached 6.6, precipitation of cuttlefish-chitosan was observed. The degree of precipitation was measured through heating gravimetric analysis.

Results: The amount of cuttlefish-chitosan dissolved in the L-aspartate buffer was 87.0% of the amount of added cuttlefish-chitosan. When the artificial intestinal juice was added until the pH of the solution reached 6.6, the ratio was 99.4%.

The amount of cuttlefish-chitosan contained in a capsule is appropriately about 30 mg as determined by the above-described tests in which an aqueous cuttlefish-chitosan solution was applied to hypertensives. However, the results of the above Test Example 1.(2) suggest that the cuttlefish-chitosan contained in a soft capsule is dissolved within the range of 45–90% in the digestive tract. Therefore, the appropriate amount of cuttlefish-chitosan to be contained in a soft capsule is considered to be 60 mg or less, twice as much as the above-described amount.

Cuttlefish-chitosan soft capsules produced in the above Example were subjected to a test involving human subjects. In general, blood pressure varies depending on climate, diet, exercise, and other habits as well as the time of day when blood pressure is measured. The susceptibility to variation in blood pressure depends greatly upon the characteristics of the individual. In order to eliminate these factors, the test was performed by use of placebos which were identical to the cuttlefish-chitosan soft capsule except that they contained no cuttlefish-chitosan powder, in accordance with a double-blind protocol in which neither doctors and patients were aware which soft capsule was administered during the test. In addition, there was employed a cross-over method in which the same patient was administered the cuttlefish-chitosan soft capsules for two weeks and the placebos for another two weeks. This rigorous comparative clinical test has proven a blood-pressure-reducing effect of the cuttlefish-chitosan soft capsule of the present invention.

Test Example 2

Effect of the Cuttlefish-Chitosan Soft Capsule on Reducing Blood Pressure of Hypertensives The test was performed on 13 hypertensives according to a double-blind cross-over protocol in which the placebos were used as a control. During the two-week administration period, two cuttlefish-chitosan soft capsules (one capsule containing 30 mg of cuttlefish-chitosan) or two placebos were orally administered daily, one capsule in the morning and the other in the evening. Blood pressure was measured and recorded twice per day during a four-week test period, upon waking up in the morning and upon retiring in the evening, for patients who were provided with a blood-pressure manometer on the wrist. The manometer is an all-in-one model wrist blood pressure manometer (product of Matsushita Denko Co.), and the patient themselves recorded the 60 measurements of blood pressure.

Figure 2:
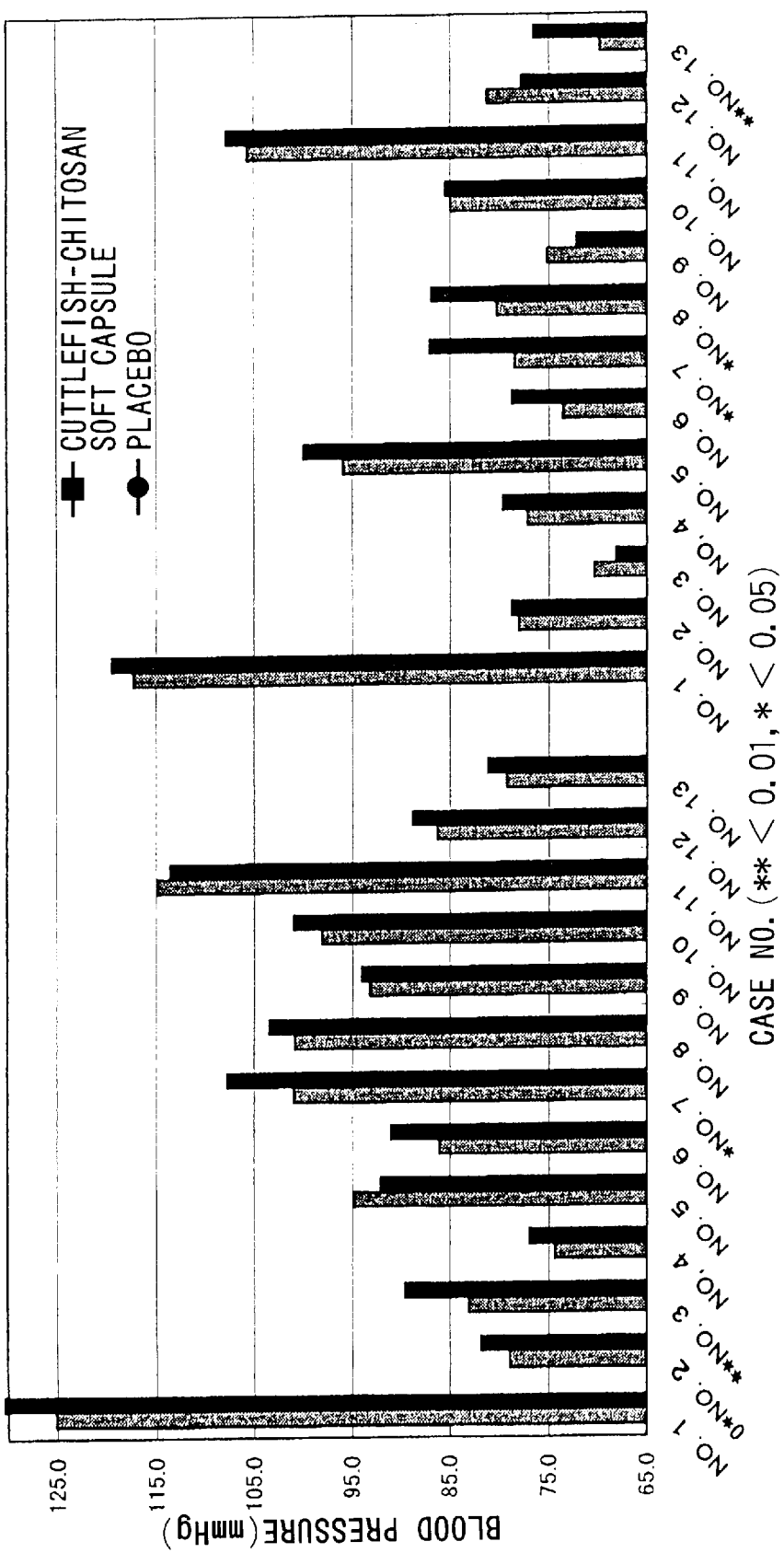
FIG. 2 is a graph showing differences in diastolic blood pressure between the case of administration of a cuttlefish-chitosan soft capsule and the case of administration of a placebo.
Figure 3:
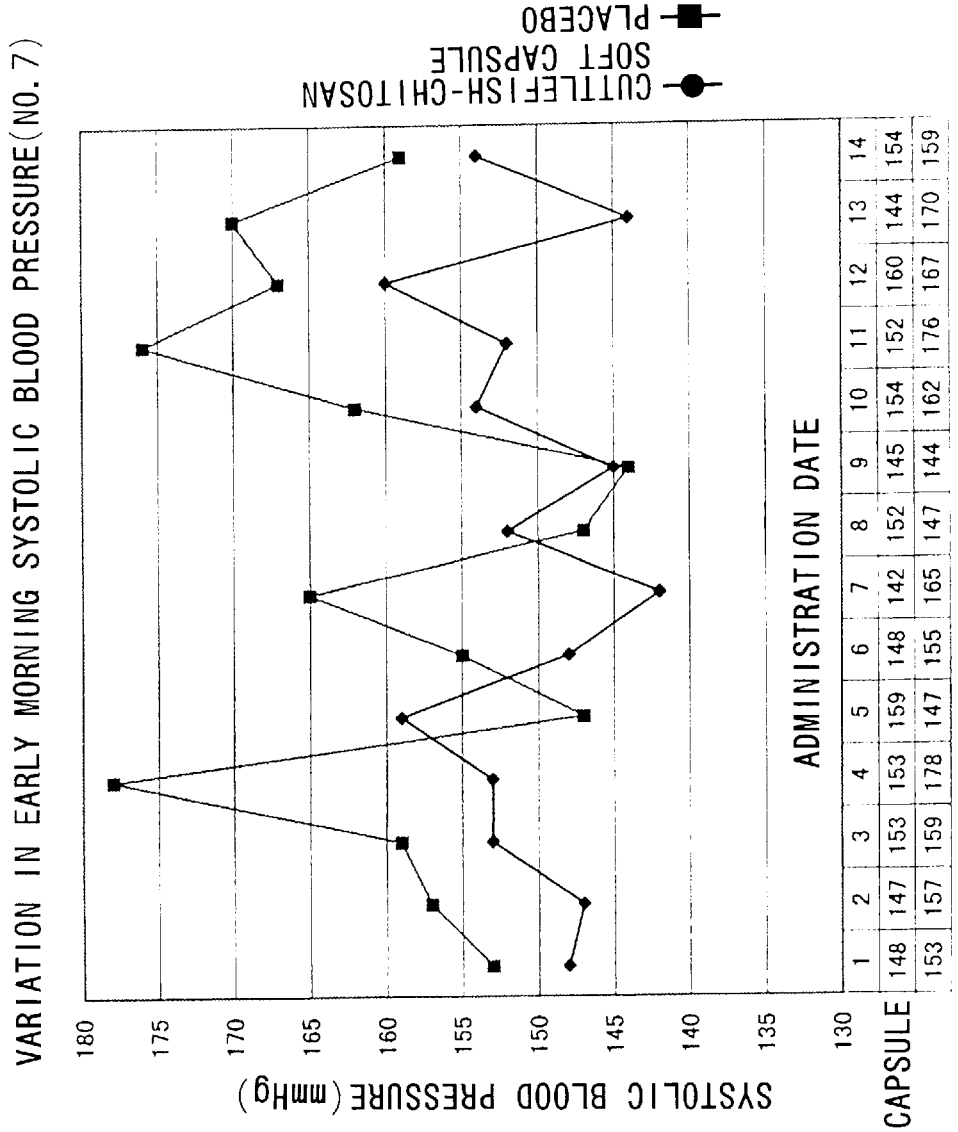
FIG. 3 is a graph showing variation in early morning systolic blood pressure of case No. 7 in Table 1.
Figure 4:
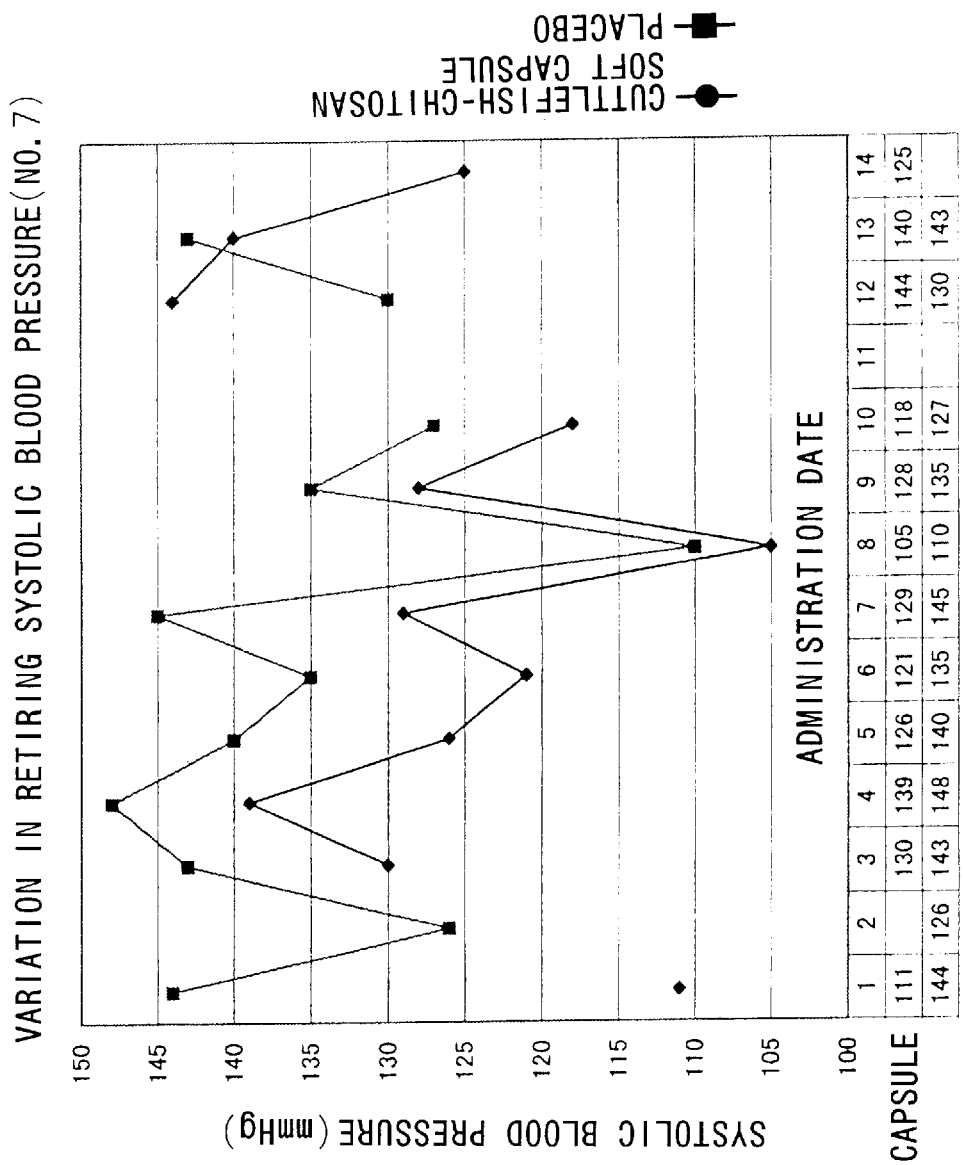
FIG. 4 is a graph showing variation in retiring (i.e., bed time) systolic blood pressure of case No. 7 in Table 1.
Figure 6:
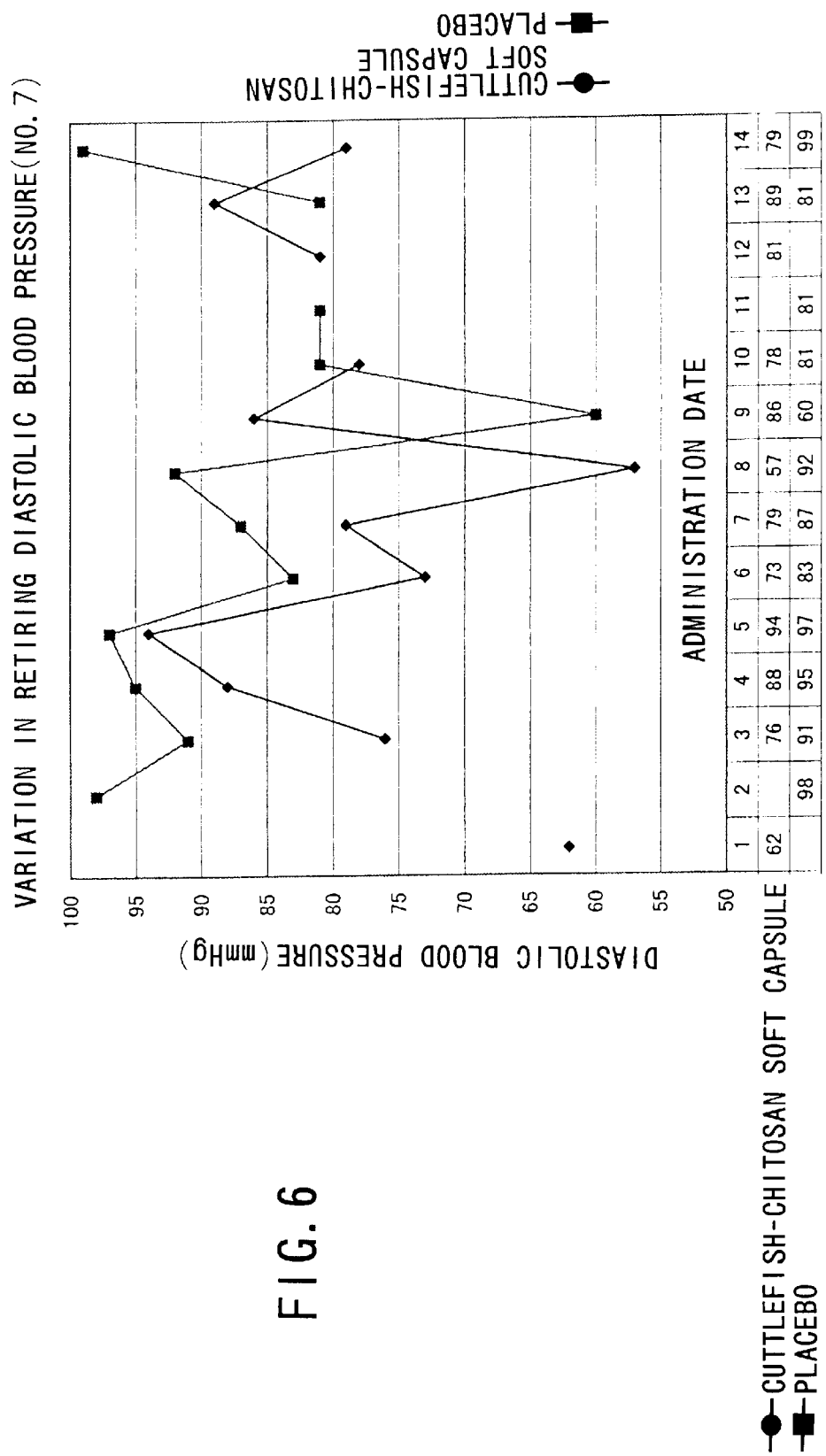
FIG. 6 is a graph showing variation in retiring (i.e., bed time) diastolic blood pressure of case No. 7 in Table 1.

Results: The average blood pressure (±SE) measured during the administration period in patients administered the cuttlefish-chitosan soft capsules and the average blood pressure (±SE) measured during the administration period in patients administered the placebos were calculated and are shown in the following Table 1.

tion period of the cuttlefish-chitosan capsule was proven to be significantly lower. For systolic blood pressure measured in the early morning, administration of the cuttlefish-chitosan capsule reduced the blood pressure in 9 cases; by as much as 7.5 mmHg or more in 5 cases. For systolic blood pressure upon retirement, as shown in FIG. 1, the blood pressure was reduced in 9 cases; by as much as 7.5 mmHg or more in 5 cases. As shown in FIG. 2, for diastolic blood pressure measured in the early morning the blood pressure was reduced in 10 cases; by as much as 5 mmHg in 4 cases.

TABLE 1

Average blood pressure for respective cases (± SE)

| Case NO. | Average blood pressure | Systolic pressure | | Diastolic pressure | |
|---|---|---|---|---|---|
| | | Morning | Night | Morning | Night |
| NO. 1 | Aminochitosan administration period (mean ± SE) | 212 ± 3.35 | 199.7 ± 6.14 | 125.1 ± 2.58 | 117.3 ± 2.79 |
| | Placebo administration period (mean ± SE) | 213.1 ± 4.57 | 207.5 ± 4.66 | 130.5 ± 2.95 | 119.5 ± 3.21 |
| NO. 2 | Aminochitosan administration period (mean ± SE) | 122.1 ± 0.73** | 124.2 ± 2.62* | 79.0 ± 0.89* | 78.1 ± 1.49 |
| | administration period (mean ± SE) | 132.5 ± 2.88 | 133.0 ± 3.25 | 81.9 ± 1.3 | 78.8 ± 0.8 |
| NO. 3 | Aminochitosan administration period (mean ± SE) | 120.8 ± 1.29* | 114.2 ± 2.66 | 83.1 ± 1.51** | 70.4 ± 2.33 |
| | administration period (mean ± SE) | 126.9 ± 2.86 | 116.9 ± 1.57 | 89.6 ± 1.9 | 68.2 ± 1.76 |
| NO. 4 | Aminochitosan administration period (mean ± SE) | 142.1 ± 6.43 | 139.7 ± 3.75** | 74.4 ± 3.2 | 77.2 ± 1.81 |
| | administration period (mean ± SE) | 150.6 ± 3.7 | 154.3 ± 2.85 | 77.0 ± 2.46 | 79.7 ± 1.37 |
| NO. 5 | Aminochitosan administration period (mean ± SE) | 133.5 ± 2.44 | 141.5 ± 2.21 | 94.9 ± 1.73 | 96 ± 3.09 |
| | administration period (mean ± SE) | 131.4 ± 1.70 | 140.7 ± 0.68 | 92.1 ± 1.49 | 100 ± 2.12 |
| NO. 6 | Aminochitosan administration period (mean ± SE) | 128.3 ± 3.4 | 126 ± 1.64* | 86.1 ± 1.91 | 73.6 ± 2.31 |
| | administration period (mean ± SE) | 135.9 ± 4.69 | 136.8 ± 4.69 | 91.1 ± 2.79 | 78.8 ± 4.16 |
| NO. 7 | Aminochitosan administration period (mean ± SE) | 150.8 ± 1.43** | 126.3 ± 3.34* | 101.9 ± 1.58* | 78.5 ± 3.11* |
| | administration period (mean ± SE) | 159.9 ± 2.81 | 135.5 ± 3.31 | 107.8 ± 2.16 | 87.1 ± 3.17 |
| NO. 8 | Aminochitosan administration period (mean ± SE) | 147.9 ± 1.6 | 128.9 ± 3.13 | 100.9 ± 0.66 | 80.3 ± 1.66* |
| | administration period (mean ± SE) | 149.4 ± 2.35 | 143.3 ± 3.27 | 103.5 ± 1.36 | 86.9 ± 3.00 |
| NO. 9 | Aminochitosan administration period (mean ± SE) | 141.1 ± 2.23 | 122.4 ± 3.09 | 93.2 ± 1.73 | 75.2 ± 2.12 |
| | administration period (mean ± SE) | 135.4 ± 3.15 | 117.5 ± 1.96 | 94.1 ± 2.55 | 72.2 ± 2.06 |
| NO. 10 | Aminochitosan administration period (mean ± SE) | 156.1 ± 3.15 | 133.7 ± 9.27 | 98.1 ± 2.17 | 85.0 ± 1.97 |
| | administration period (mean ± SE) | 157.9 ± 2.49 | 139.7 ± 2.79 | 101.0 ± 1.17 | 85.5 ± 2.82 |
| NO. 11 | Aminochitosan administration period (mean ± SE) | 163.3 ± 1.68 | 159.1 ± 2.04 | 114.9 ± 1.15 | 105.7 ± 2.00 |
| | administration period (mean ± SE) | 162.5 ± 1.68 | 158.7 ± 2.39 | 113.6 ± 0.56 | 107.8 ± 1.31 |
| NO. 12 | Aminochitosan administration period (mean ± SE) | 130.8 ± 1.98* | 126.6 ± 1.95 | 86.3 ± 0.98 | 81.3 ± 1.08 |
| | administration period (mean ± SE) | 139.4 ± 3.03 | 123.5 ± 2.07 | 88.8 ± 1.17 | 77.8 ± 1.73 |
| NO. 13 | Aminochitosan administration period (mean ± SE) | 154.5 ± 2.53 | 142 ± 3.4 | 79.3 ± 1.55 | 69.8 ± 1.50** |
| | administration period (mean ± SE) | 149.2 ± 1.76 | 147.1 ± 2.56 | 81.2 ± 1.08 | 76.6 ± 1.61 |
| All cases | Aminochitosan administration period (mean ± SE) | 145.7** | 137.3** | 93.6** | 83.7* |
| | administration period (mean ± SE) | 149.5 | 142.7 | 96.3 | 86.1 |

**<0.01, *<0.05(T-test)

A reduction in systolic pressure of 7.5 mmHg or more by administration of the cuttlefish-chitosan capsule or a reduction in diastolic pressure of 5 mmHg or more by the administration of the same is considered amelioration. As a result, among 13 cases, 9 cases were ameliorated. The results are shown in the following Table 2.

TABLE 2

Effect of the cuttlefish-chitosan capsule on reduction of blood pressure

| Amelioration* | No change | Aggravation | Total cases |
|---|---|---|---|
| 9 | 4 | 0 | 13 |

$p < 0.05$
*A reduction in average systolic pressure of 7.5 mmHg or more by administration of the cuttlefish-chitosan capsule or a reduction in average diastolic pressure of 5 mmHg or more by administration of the same is considered amelioration.

The results were recognized to represent amelioration having statistical significance. In addition, when the average blood pressure measured during the administration period of the cuttlefish-chitosan capsule was compared with the average blood pressures measured in the administration period of the placebo, the blood pressure measured in the administra- FIGS. 3 through 6 show the variance in the blood pressure of a typical case, No. 7 in Table 1. As is apparent from the Figures, during the administration period the blood pressure of the patients administered cuttlefish-chitosan capsule was lower and more stable than that of the patients administered the placebo.

When the administration of the cuttlefish-chitosan capsule was started, in some cases blood pressure was reduced from the next day. The assumed reason for this phenomenon is that the cuttlefish-chitosan capsule has an effect on suppression of absorption of salt and reduction of ACE activity in the blood. Since patients can instantly realizes the effect of administration, they are encouraged to continue taking the capsules. Thus, use of the capsule as a pharmaceutical or a health food is advantageous in practice.

Prior to the test conducted on human subjects, the present inventors confirmed the safety of cuttlefish-chitosan. Forced administration of water-soluble cuttlefish-chitosan in an amount of 30 mg or less (3 ml of 1% solution) to SD rats was performed for 7 days. Investigation of the effects on general health, body weight, and blood biochemistry has proven that there is no particular effect on body weight or blood biochemistry.

Test Example 3

Safety Test of Aqueous Cuttlefish-Chitosan Solution in Rats

Effects of an aqueous cuttlefish-chitosan solution on body weight and on the blood biochemistry were investigated.

Method: 7-week-old SD male rats were divided into 5 groups (n=8). For 7 continuous days the respective groups were administered an aqueous cuttlefish-chitosan solution in an amount of 0.5 ml, 1 ml, 2 ml, and 3 ml, and distilled water alone in an amount of 2 ml. (control group). Before and after administration body weight was measured, along with amounts of glucose, total protein, albumin, GOT, GPT, alkaline phosphatase, amylase, total cholesterol, BUN, creatinine, uric acid, Ca, P, Na, K, and Cl. Blood was collected after 6 hours of fasting. Blood collection was also carried out 24 hours after administration of the cuttlefish-chitosan.

Results: No significant difference was found between the groups administered an aqueous solution of cuttlefish-chitosan in an amount of 3, 2, 1, and 0.5 ml and the control group in terms of body weight, glucose, total protein, albumin, GOT, GPT, alkaline phosphatase, amylase, total cholesterol, BUN, creatinine, uric acid, Ca, P, Na, K, and Cl. In addition, examination of general symptoms showed no difference between the test groups and the control group.

Chitosan is generally known to also be effective in treatment for hyperlipemia, hyperuricemia, allergic diseases such as asthma and atopy, and lowering of immunity caused by cancer, in addition to hypertension. Furthermore, chitosan is known to have an effect on suppression absorption of fat from food in the digestive tract. The present invention is also applicable to these objects.

As described hereinabove, although chitosan has already been known to provide an effect on reduction of blood pressure, when chitosan is used as a pharmaceutical or health food, a 3–5 g dosage of chitosan is required, thereby raising a considerable practical problem. Conventionally, it has been accepted that $Cl^-$ in food is captured by chitosan in the digestive tract and is excreted into feces, resulting in reduction of blood pressure. The present inventors have proposed a new concept that the chitosan molecule inhibits an absorption process of $Cl^-$ such as $Cl^-$ channeling. Accordingly, based on the idea that even less chitosan will be able to control blood pressure, a lower dosage of water-soluble chitosan was provided for hypertensives and the effect on reducing blood pressure was confirmed. However, an aqueous solution of chisaton has a highly disagreeable taste and therefore has involved difficulty in a practical application as a pharmaceutical or health food. Thus, encapsulation of a chisaton aqueous solution was attempted in vain. After careful studies, the inventors succeeded to invent a soft capsule containing powdery chitosan which becomes water-soluble in the digestive tract. Furthermore, a clinical test confirmed that the present invention is useful for controlling blood pressure of hypertensives. The present invention is a useful ingredient for safe and effective pharmaceuticals or health food for hypertensives.

What is claimed is:

1. A process for producing a chitosan-containing soft capsule comprising the following steps:
    rendering chitosan into a powder;
    adding the chitosan powder, powder comprising an organic acid and a salt thereof, and an emulsifier to an oil or fat;
    stirring the resultant mixture so as to suspend the powders, to thereby obtain a suspension; and
    feeding the suspension and a gelatin solution for coating into an automated encapsulation machine, to effect encapsulation of the stock with gelatin.

2. The process according to claim 1, wherein the organic acid is an amino acid.

3. The process according to claim 1, wherein the organic acid and a salt thereof are glutamic acid and sodium glutamate.

4. The process according to claim 1, wherein the oil or fat is soybean oil, sesame oil, olive oil, rapeseed oil, cottonseed oil, rice oil, corn oil, evening primrose oil, safflower oil, palm oil, castor oil, sardine oil, herring oil, cod oil, shark oil, cuttlefish oil, whale oil, dolphin oil, roach oil, carp oil, eel oil, hyperoratia oil, euphausian oil, chrysalis oil, lard, or beef tallow.

5. The process according to claim 1, wherein the chitosan is derived from cuttlefish.

6. A chitosan-containing soft capsule comprising a capsule enclosing a composition which contains chitosan powder and powder comprising an organic acid and a salt thereof suspended in an emulsifier-added oil or fat.

7. The chitosan-containing soft capsule according to claim 6, wherein the organic acid is an amino acid.

8. The chitosan-containing soft capsule according to claim 6, wherein the organic acid and the salt are glutamic acid and sodium glutamate.

9. The chitosan-containing soft capsule according to claim 6, wherein the oil or fat is selected from the group consisting of soybean oil, sesame oil, olive oil, rapeseed oil, cottonseed oil, rice oil, corn oil, evening primrose oil, safflower oil, palm oil, castor oil, sardine oil, herring oil, cod oil, shark oil, cuttlefish oil, whale oil, dolphin oil, roach oil, carp oil, eel oil, hyperoratia oil, euphausian oil, chrysalis oil, lard, and beef tallow.

10. The chitosan-containing soft capsule according to claim 1, wherein the chitosan is derived from cuttlefish.

11. The process according to claim 2, wherein the amino acid is selected from the group consisting of glutamic acid, aspartic acid, a hydroxycarboxylic acid, and a pyrrolidonecarboxylic acid.

12. The chitosan-containing soft capsule according to claim 8, wherein the organic acid is an amino acid selected from the group consisting of glutamic acid, aspartic acid, a hydroxycarboxylic acid, and a pyrrolidonecarboxylic acid.

* * * * *